(12) United States Patent
Briganti et al.

(10) Patent No.: US 7,942,888 B2
(45) Date of Patent: May 17, 2011

(54) VASCULAR HOLE CLOSURE DEVICE

(75) Inventors: Richard T. Briganti, Conshohocken, PA (US); James F. McGuckin, Jr., Radnor, PA (US); James S. Tarmin, Philadelphia, PA (US); Walter H. Peters, Downingtown, PA (US)

(73) Assignee: Rex Medical, L.P., Conshohocken, PA (US)

( * ) Notice: Subject to any disclaimer, the term of this patent is extended or adjusted under 35 U.S.C. 154(b) by 988 days.

(21) Appl. No.: 11/324,625

(22) Filed: Jan. 3, 2006

(65) Prior Publication Data
US 2006/0155327 A1    Jul. 13, 2006

Related U.S. Application Data (63) Continuation-in-part of application No. 10/847,141, filed on May 17, 2004, now Pat. No. 7,662,161, which is a continuation-in-part of application No. 10/345,533, filed on Jan. 16, 2003, now Pat. No. 7,267,679, which is a continuation-in-part of application No. 10/163,142, filed on Jun. 5, 2002, now Pat. No. 7,341,595, and a continuation-in-part of application No. 09/659,648, filed on Sep. 12, 2000, now abandoned.

(60) Provisional application No. 60/643,907, filed on Jan. 14, 2005, provisional application No. 60/355,526, filed on Feb. 6, 2002, provisional application No. 60/153,736, filed on Sep. 13, 1999.

(51) Int. Cl.
*A61B 17/08* (2006.01)
*A61D 1/00* (2006.01)

(52) U.S. Cl. .......................................... 606/151; 606/213
(58) Field of Classification Search .................. 606/151, 606/157, 213, 215, 219, 220; 411/340–345; 128/832
See application file for complete search history.

(56) References Cited

U.S. PATENT DOCUMENTS

| | | | |
|---|---|---|---|
| 2,024,871 A * | 12/1935 | Parsons | 411/342 |
| 2,398,220 A * | 4/1946 | Gelpcke | 411/342 |
| 3,527,223 A | 9/1970 | Melvin | |
| 3,874,388 A | 4/1975 | King et al. | |
| 3,937,217 A | 2/1976 | Kosonen | |
| 3,958,576 A | 5/1976 | Komiya | |
| 4,007,743 A | 2/1977 | Blake | |
| 4,031,569 A | 6/1977 | Jacob | |
| 4,117,838 A | 10/1978 | Hasson | |
| 4,286,497 A * | 9/1981 | Shamah | 411/342 |
| 4,317,445 A | 3/1982 | Robinson | |
| 4,485,816 A | 12/1984 | Krumme | |
| 4,505,274 A | 3/1985 | Speelman | |

(Continued)

FOREIGN PATENT DOCUMENTS
DE    19604817    8/1997

(Continued)

*Primary Examiner* — Darwin P Erezo
*Assistant Examiner* — Dianne Dornbusch
(74) *Attorney, Agent, or Firm* — Neil D. Gershon (57) ABSTRACT

A device for closing an aperture in a vessel wall comprising a covering member having a longitudinal axis and positionable inside the vessel against the internal opening of the aperture and having a dimension to prevent egress of fluid through the aperture. Two curved legs are provided having portions positionable external of the vessel and curving in different directions. At least one retention member is positioned between the covering member and curved legs and positionable external of the vessel.

15 Claims, 10 Drawing Sheets

U.S. PATENT DOCUMENTS

| | | | |
|---|---|---|---|
| 4,512,338 A | 4/1985 | Balko et al. | |
| 4,610,671 A | 9/1986 | Luther | |
| 4,615,514 A * | 10/1986 | Hamlin | 269/41 |
| 4,638,803 A | 1/1987 | Rand | |
| 4,665,906 A | 5/1987 | Jervis | |
| 4,676,245 A | 6/1987 | Eukuda | |
| 4,744,364 A | 5/1988 | Kensey | |
| 4,836,204 A | 6/1989 | Landymore et al. | |
| 4,917,089 A | 4/1990 | Sideris | |
| 4,924,866 A | 5/1990 | Yoon | |
| 4,971,068 A | 11/1990 | Sahi | |
| 5,021,059 A | 6/1991 | Kensey et al. | |
| 5,047,047 A | 9/1991 | Yoon | |
| 5,061,274 A | 10/1991 | Kensey | |
| 5,108,420 A | 4/1992 | Marks | |
| 5,171,252 A | 12/1992 | Friedland | |
| 5,171,259 A | 12/1992 | Inoue | |
| 5,192,300 A | 3/1993 | Fowler | |
| 5,192,301 A | 3/1993 | Kamilya et al. | |
| 5,192,302 A | 3/1993 | Kensey et al. | |
| 5,222,974 A | 6/1993 | Kensey et al. | |
| 5,246,441 A | 9/1993 | Ross et al. | |
| 5,279,572 A | 1/1994 | Hokama | |
| 5,282,827 A | 2/1994 | Kensey et al. | |
| 5,306,254 A | 4/1994 | Nash et al. | |
| 5,312,435 A | 5/1994 | Nash et al. | |
| 5,334,210 A | 8/1994 | Gianturco | |
| 5,350,399 A | 9/1994 | Erlebacher et al. | |
| 5,350,400 A | 9/1994 | Esposito et al. | |
| 5,385,554 A | 1/1995 | Brimhall | |
| RE34,866 E | 2/1995 | Kensey et al. | |
| 5,391,183 A | 2/1995 | Janzen et al. | |
| 5,411,520 A | 5/1995 | Nash et al. | |
| 5,441,517 A | 8/1995 | Kensey et al. | |
| 5,443,481 A | 8/1995 | Lee | |
| 5,451,235 A | 9/1995 | Lock et al. | |
| 5,474,557 A | 12/1995 | Mai | |
| 5,478,352 A | 12/1995 | Fowler | |
| 5,478,353 A | 12/1995 | Yoon | |
| 5,486,195 A | 1/1996 | Myers et al. | |
| 5,531,759 A | 7/1996 | Kensey et al. | |
| 5,540,716 A | 7/1996 | Hlavacek | |
| 5,545,178 A | 8/1996 | Kensey et al. | |
| 5,549,633 A | 8/1996 | Evans et al. | |
| 5,591,204 A | 1/1997 | Janzen et al. | |
| 5,593,422 A | 1/1997 | Muijs Van de Moer et al. | |
| 5,620,461 A | 4/1997 | Muijs Van De Moer et al. | |
| 5,630,833 A | 5/1997 | Katsaros et al. | |
| 5,634,936 A | 6/1997 | Linden et al. | |
| 5,643,317 A | 7/1997 | Pavcnik et al. | |
| 5,649,959 A | 7/1997 | Hannam et al. | |
| 5,662,681 A * | 9/1997 | Nash et al. | 606/213 |
| 5,674,231 A | 10/1997 | Green et al. | |
| 5,676,689 A | 10/1997 | Kensey et al. | |
| 5,690,674 A | 11/1997 | Diaz | |
| 5,700,277 A | 12/1997 | Nash et al. | |
| 5,702,421 A | 12/1997 | Schneidt | |
| 5,707,393 A | 1/1998 | Kensey et al. | |
| 5,709,707 A | 1/1998 | Lock et al. | |
| 5,725,498 A | 3/1998 | Janzen et al. | |
| 5,728,132 A | 3/1998 | Van Tassel et al. | |
| 5,728,133 A | 3/1998 | Kontos | |
| 5,741,297 A | 4/1998 | Simon | |
| 5,782,860 A | 7/1998 | Epstein et al. | |
| 5,782,861 A | 7/1998 | Cragg et al. | |
| 5,810,846 A | 9/1998 | Virnich et al. | |
| 5,810,884 A * | 9/1998 | Kim | 606/213 |
| 5,820,628 A | 10/1998 | Middleman et al. | |
| 5,861,003 A | 1/1999 | Latson et al. | |
| 5,893,856 A * | 4/1999 | Jacob et al. | 606/151 |
| 5,910,155 A | 6/1999 | Ratcliff et al. | |
| 5,916,003 A | 6/1999 | Masini et al. | |
| 5,916,236 A | 6/1999 | Muijs Van de Moer et al. | |
| 5,919,207 A | 7/1999 | Taheri | |
| 5,964,782 A | 10/1999 | Lafontaine et al. | |
| 5,976,159 A | 11/1999 | Bolduc et al. | |
| 5,976,174 A | 11/1999 | Ruiz | |
| 5,984,949 A | 11/1999 | Levin | |
| 6,001,110 A | 12/1999 | Adams | |
| 6,007,563 A | 12/1999 | Nash et al. | |
| 6,010,517 A | 1/2000 | Baccaro | |
| 6,015,417 A | 1/2000 | Reynolds | |
| 6,033,427 A | 3/2000 | Lee | |
| 6,048,357 A | 4/2000 | Kontos | |
| 6,048,358 A | 4/2000 | Barak | |
| 6,056,768 A | 5/2000 | Cates et al. | |
| 6,063,085 A | 5/2000 | Tay et al. | |
| 6,071,300 A | 6/2000 | Brenneman et al. | |
| 6,077,281 A | 6/2000 | Das | |
| 6,080,182 A | 6/2000 | Shaw et al. | |
| 6,080,183 A | 6/2000 | Tsugita et al. | |
| 6,113,611 A | 9/2000 | Allen et al. | |
| 6,117,159 A | 9/2000 | Huebsch et al. | |
| 6,120,524 A | 9/2000 | Taheri | |
| 6,139,564 A | 10/2000 | Teoh | |
| 6,171,320 B1 | 1/2001 | Monassevitch | |
| 6,171,329 B1 | 1/2001 | Shaw et al. | |
| 6,174,322 B1 | 1/2001 | Schneidt | |
| 6,179,863 B1 | 1/2001 | Kensey | |
| 6,197,042 B1 | 3/2001 | Ginn et al. | |
| 6,206,907 B1 | 3/2001 | Marino et al. | |
| 6,228,096 B1 | 5/2001 | Marchand | |
| 6,231,561 B1 | 5/2001 | Frazier et al. | |
| 6,251,122 B1 | 6/2001 | Tsukernik | |
| 6,261,309 B1 | 7/2001 | Urbanski | |
| 6,270,515 B1 | 8/2001 | Linden et al. | |
| 6,277,140 B2 | 8/2001 | Ginn et al. | |
| 6,328,727 B1 | 12/2001 | Frazier et al. | |
| 6,334,865 B1 | 1/2002 | Redmond et al. | |
| 6,336,914 B1 | 1/2002 | Gillespie | |
| 6,342,064 B1 | 1/2002 | Koike et al. | |
| 6,346,117 B1 | 2/2002 | Greenhalgh | |
| 6,350,270 B1 | 2/2002 | Roue | |
| 6,350,274 B1 | 2/2002 | Li | |
| 6,355,052 B1 | 3/2002 | Neuss | |
| 6,368,341 B1 | 4/2002 | Abrahamson | |
| 6,391,037 B1 | 5/2002 | Greenhalgh | |
| 6,391,048 B1 | 5/2002 | Ginn et al. | |
| 6,409,739 B1 | 6/2002 | Nobels et al. | |
| 6,419,669 B1 | 7/2002 | Frazier et al. | |
| 6,425,911 B1 * | 7/2002 | Akerfeldt et al. | 606/213 |
| 6,436,088 B2 | 8/2002 | Frazier et al. | |
| 6,447,524 B1 | 9/2002 | Knodel et al. | |
| 6,482,179 B1 | 11/2002 | Chu et al. | |
| 6,508,828 B1 | 1/2003 | Akerfeldt et al. | |
| 6,537,299 B1 | 3/2003 | Hogendijk et al. | |
| 6,569,185 B2 | 5/2003 | Ungs | |
| 6,585,748 B1 | 7/2003 | Jeffree | |
| 6,596,012 B2 | 7/2003 | Akerfeldt et al. | |
| 6,626,937 B1 | 9/2003 | Cox | |
| 6,682,489 B2 | 1/2004 | Tenerz et al. | |
| 6,712,837 B2 | 3/2004 | Akerfeldt et al. | |
| 6,749,621 B2 | 6/2004 | Pantages et al. | |
| 6,766,186 B1 | 7/2004 | Hoyns et al. | |
| 6,786,915 B2 | 9/2004 | Akerfeldt et al. | |
| 6,790,220 B2 | 9/2004 | Morris | |
| 6,846,316 B2 | 1/2005 | Abrams | |
| 6,855,153 B2 | 2/2005 | Saadat | |
| 6,960,224 B2 | 11/2005 | Marino et al. | |
| 7,025,776 B1 | 4/2006 | Houser et al. | |
| 7,033,393 B2 | 4/2006 | Gainor et al. | |
| 7,153,323 B1 | 12/2006 | Teoh et al. | |
| 7,618,438 B2 | 11/2009 | White et al. | |
| 2002/0082622 A1 | 6/2002 | Kane | |
| 2002/0165572 A1 | 11/2002 | Saadat | |
| 2003/0055451 A1 | 3/2003 | Jones et al. | |
| 2003/0088269 A1 | 5/2003 | Ashby | |
| 2003/0105487 A1 | 6/2003 | Bemz et al. | |
| 2003/0187473 A1 | 10/2003 | Berenstein et al. | |
| 2003/0191495 A1 * | 10/2003 | Ryan et al. | 606/213 |
| 2004/0002764 A1 * | 1/2004 | Gainor et al. | 623/17.16 |
| 2004/0143294 A1 | 7/2004 | Corcoran et al. | |
| 2004/0153103 A1 | 8/2004 | Schwartz et al. | |

| | | |
|---|---|---|
| 2004/0158287 A1 | 8/2004 | Cragg et al. |
| 2005/0055027 A1* | 3/2005 | Yeung et al. .................. 606/75 |
| 2005/0065547 A1 | 3/2005 | Marino et al. |
| 2005/0070957 A1 | 3/2005 | Das |
| 2005/0085852 A1 | 4/2005 | Ditter |
| 2005/0090859 A1 | 4/2005 | Ravlkumar |
| 2005/0107807 A1 | 5/2005 | Nakao |
| 2005/0192627 A1 | 9/2005 | Whisenant et al. |
| 2005/0267524 A1 | 12/2005 | Chanduszko |
| 2006/0106418 A1 | 5/2006 | Seibold et al. |
| 2006/0173492 A1 | 8/2006 | Akerfeldt et al. |
| 2007/0149998 A1 | 6/2007 | Wicks et al. |

FOREIGN PATENT DOCUMENTS

| | | |
|---|---|---|
| EP | 0637431 | 2/1995 |
| EP | 0920842 | 6/1999 |
| WO | 9520916 | 8/1995 |
| WO | 9707741 | 3/1997 |
| WO | 9827868 | 7/1998 |
| WO | 9900055 | 1/1999 |
| WO | 9905977 | 2/1999 |
| WO | 9938454 | 8/1999 |
| WO | 2004012601 | 2/2004 |
| WO | 2004112864 | 12/2004 |

* cited by examiner

FIG_1

FIG_1A

FIG_2

FIG_5

FIG. 7

VASCULAR HOLE CLOSURE DEVICE

This application claims priority from provisional application No. 60/643,907, filed Jan. 14, 2005 and is a continuation-in-part of patent application Ser. No. 10/847,141, filed May 17, 2004, now U.S. Pat. No. 7,662,161 which is a continuation-in-part of application Ser. No. 10/345,533, filed Jan. 16, 2003, now U.S. Pat. No. 7,267,679, which is a continuation-in-part of application Ser. No. 10/163,142, filed Jun. 5, 2002, now U.S. Pat. No. 7,341,595, which claims priority from provisional application Ser. No. 60/355,526, filed Feb. 6, 2002 and which is a continuation-in-part of application Ser. No. 09/659,648, filed Sep. 12, 2000, now abandoned which claims priority from provisional patent application Ser. No. 60/153,736, filed Sep. 13, 1999. The entire contents of each of these applications are incorporated herein by reference in their entirety.

BACKGROUND

1. Technical Field

This application relates to a vascular device and more particularly to a device for closing openings in vessel walls.

2. Background of Related Art

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery.

Several approaches to date have been used to close femoral access holes. In one approach, manual compression by hand over the puncture site is augmented by a sandbag or weight until the blood coagulates. With this approach, it can take up to six hours for the vessel hole to close and for the patient to be able to ambulate. This inefficiency increases the surgical procedure time as well as the overall cost of the procedure since the hospital staff must physically maintain pressure and the patient's discharge is delayed because of the inability to ambulate.

In another approach to close the vessel puncture site, a clamp is attached to the operating table and the patient's leg. The clamp applies pressure to the vessel opening. The patient, however, must still be monitored to ensure the blood is coagulating, requiring additional time of the hospital staff and increasing the cost of the procedure.

To avoid the foregoing disadvantages of manual pressure approaches, suturing devices have been developed. One such suturing device, referred to as "the Closer" and sold by Perclose, advances needles adjacent the vessel wall opening and pulls suture material outwardly through the wall adjacent the opening. The surgeon then ties a knot in the suture, closing the opening. One difficulty with the procedure involves the number of steps required by the surgeon to deploy the needles, capture the suture, withdraw the suture, and tie the knot and secure the suture. Moreover, the surgeon cannot easily visualize the suture because of the depth of the femoral artery (relative to the skin) and essentially ties the suture knot blindly or blindly slips a pre-tied knot into position. Additionally, the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system. It is also difficult to pass the needle through calcified vessels.

U.S. Pat. No. 4,744,364 discloses another approach for sealing a vessel puncture in the form of a device having an expandable closure member with a filament for pulling it against the vessel wall. The closure member is held in place by a strip of tape placed on the skin to hold the filament in place. However, the closure device is still subject to movement which can cause leakage through the puncture. Additionally, if the suture becomes loose, the closure member is not retained and can flow downstream in the vessel. Moreover, since the suture extends through the skin, a potential pathway for infection is created. The closure device in U.S. Pat. No. 5,545,178 includes a resorbable collagen foam plug located within the puncture tract. However, since coagulation typically takes up to twenty minutes and blood can leak in between the plug and tissue tract, manual pressure must be applied to the puncture for a period of time, until the collagen plug expands within the tract.

It would therefore be advantageous to provide a device which would more quickly and effectively close openings (punctures) in vessel walls. Such device would advantageously avoid the aforementioned time and expense of applying manual pressure to the opening, simplify the steps required to close the opening, avoid widening of the opening, and more effectively retain the closure device in the vessel.

Commonly assigned co-pending patent application Ser. No. 10/847,141, filed May 17, 2004, discloses effective vascular hole closure devices which have the foregoing advantages. It would be further advantageous to provide a hole closure device which provides the additional advantage of further restricting movement of the device upon placement to close the vessel opening.

SUMMARY

The present invention overcomes the disadvantages and deficiencies of the prior art. The present invention provides a device for closing an aperture in a vessel wall having an external opening in an external region of the vessel wall and an internal opening in an internal region of the vessel wall. The device comprises a covering member having a longitudinal axis and positionable inside the vessel against the internal opening of the aperture and having a dimension to prevent egress of fluid through the aperture. Two curved legs are provided having portions positionable external of the vessel and curving in different directions. At least one retention member is positioned between the covering member and curved legs and is positionable external of the vessel.

In a preferred embodiment, the two curved legs are fabricated from a unitary material. Preferably, the curved legs are composed of shape memory metal material and the covering member is composed of a resorbable material. In a preferred embodiment, the retention member is composed of shape memory metal material, has a memorized position extending transverse to an axis transverse to a longitudinal axis of the covering member, and is fabricated from the unitary material which forms the curved legs. In a preferred embodiment, the retention member extends at an angle toward the covering member to limit movement of the device into the vessel once the device is positioned to close the aperture in the vessel wall. In a preferred embodiment, the retention member and curved legs are delivered to the vessel wall in a substantially straightened position.

In one embodiment, a second retention member is positioned between the covering member and curved legs and positionable external of the vessel. The retention members preferably extend at an angle transverse to an axis transverse to the longitudinal axis of the covering member. The retention members preferably extend in substantially the same direction.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1:
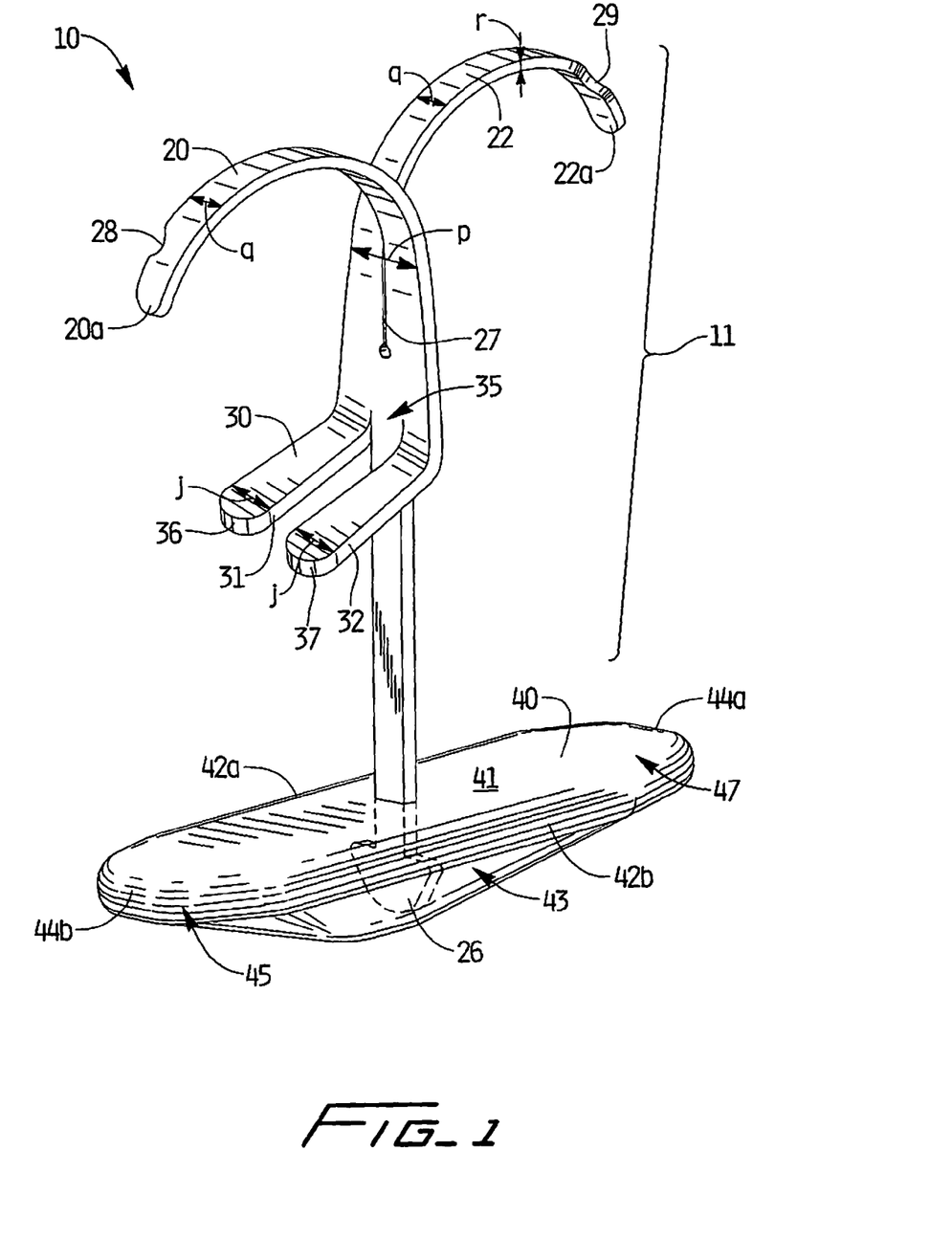
FIG. 1 is a perspective view of a first embodiment of the closure device of the present invention showing the clip legs and retention tabs in their memorized position.

Referring now in detail to the drawings where like reference numerals identify similar or like components throughout the several views, FIG. 1 is a perspective view of a first embodiment of the vascular hole (aperture) closure device of the present invention. The device is intended to close an aperture in the vessel wall, typically formed after removal of a catheter previously inserted through the vessel wall into the vessel lumen for performing angioplasty or other interventional procedures. The aperture extends through the patient's skin and underlying tissue, through the external wall of the vessel, through the wall of the vessel, and through the internal wall of the vessel to communicate with the internal lumen of the vessel. The closure devices of the present invention have a covering member or patch positioned within the vessel positioned against the internal wall of the vessel to block blood flow and a clip positioned external of the vessel wall to retain the covering member. The clip pulls the covering member upwardly towards the aperture. The device further includes a retention tab(s) also positioned external of the vessel, but closer to the vessel wall, and preferably in abutment with the external wall of the vessel or tissue abutting the external vessel wall, to limit movement of the device towards the vessel aperture once the closure device is in position to close the aperture. Thus, movement of the patch away from the internal wall of the vessel is restricted.

Turning first to FIGS. 1-5, a first embodiment of the closure device of the present invention is illustrated. Hole (aperture) closure device 10 has a covering member or patch 40 and a clip portion 11 having two legs 20 and 22 and two retention tabs or members 30 and 32. The covering member 40 is dimensioned and configured for positioning inside the vessel on the internal side of the vessel aperture against the internal wall of the vessel; the legs 20, 22 are configured to be positioned outside the vessel wall proximal the external side of the vessel aperture; and the tabs 30, 32 are configured to be positioned on the external side of the vessel aperture adjacent or against the external wall of the vessel.

Covering member 40, preferably elongated in configuration as shown, is retained in a delivery tube in a longitudinal position for delivery to the vessel, and then pivots to a transverse position within the vessel lumen (substantially perpendicular to an axis extending through the aperture), for orientation to cover (patch) the vessel aperture on the internal side. This movement is illustrated in FIGS. 37A-37D of commonly assigned co-pending patent application Ser. No. 10/847,141, filed May 17, 2004, the entire contents of which are incorporated herein by reference.

Figure 4A:
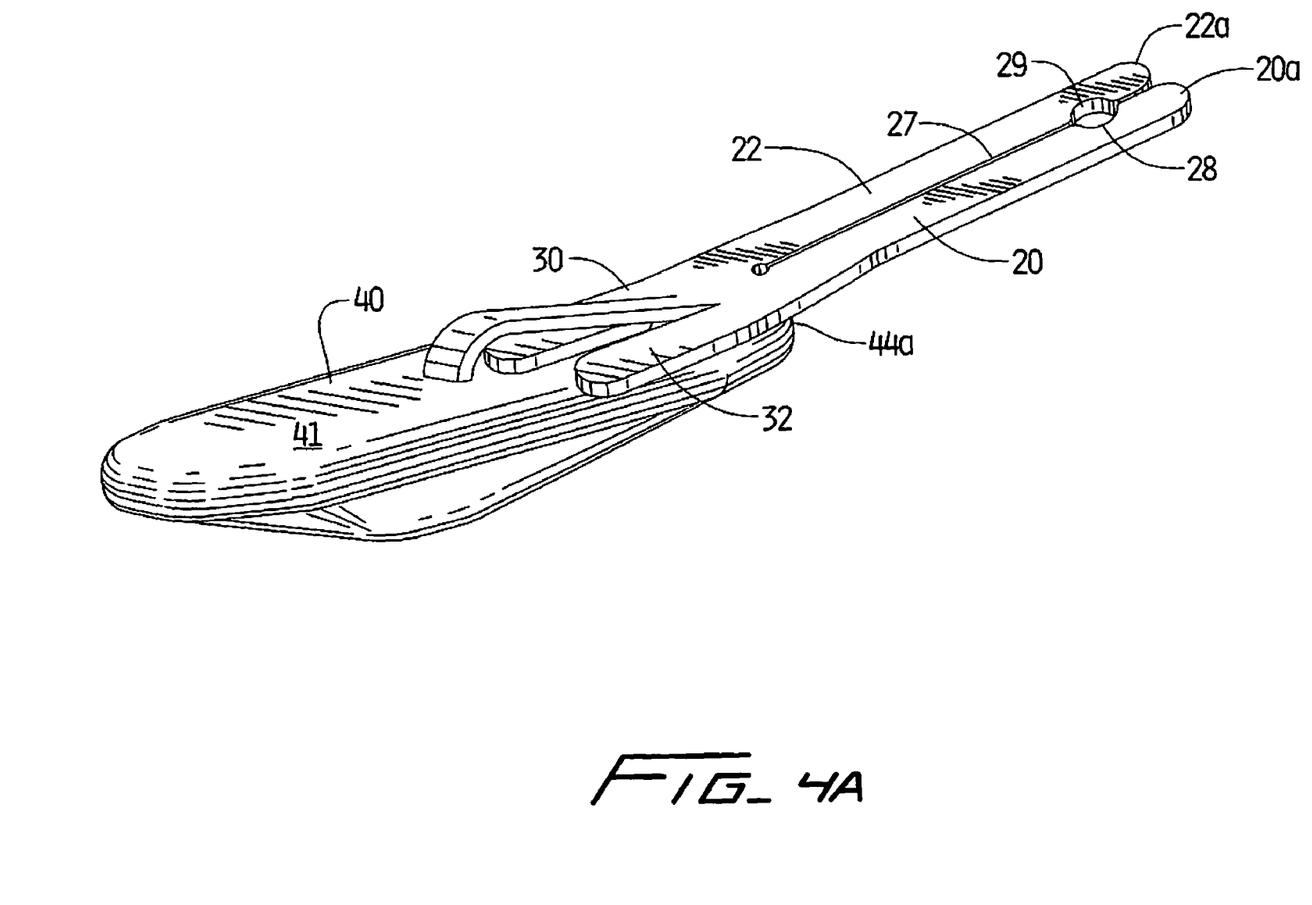
FIG. 4A is a perspective view showing the closure device of FIG. 1 in the delivery position.

The clip legs 20, 22 and tabs 30, 32 are retained in the delivery tube in an elongated substantially straightened position for delivery to the vessel. This delivery position is illustrated in FIG. 4A. They are preferably composed of shape memory material and preferably maintained in this straightened martensitic position (during delivery) by the injection of cold saline. When released from the delivery tube, they move toward their memorized position as described below.

Figure 3:
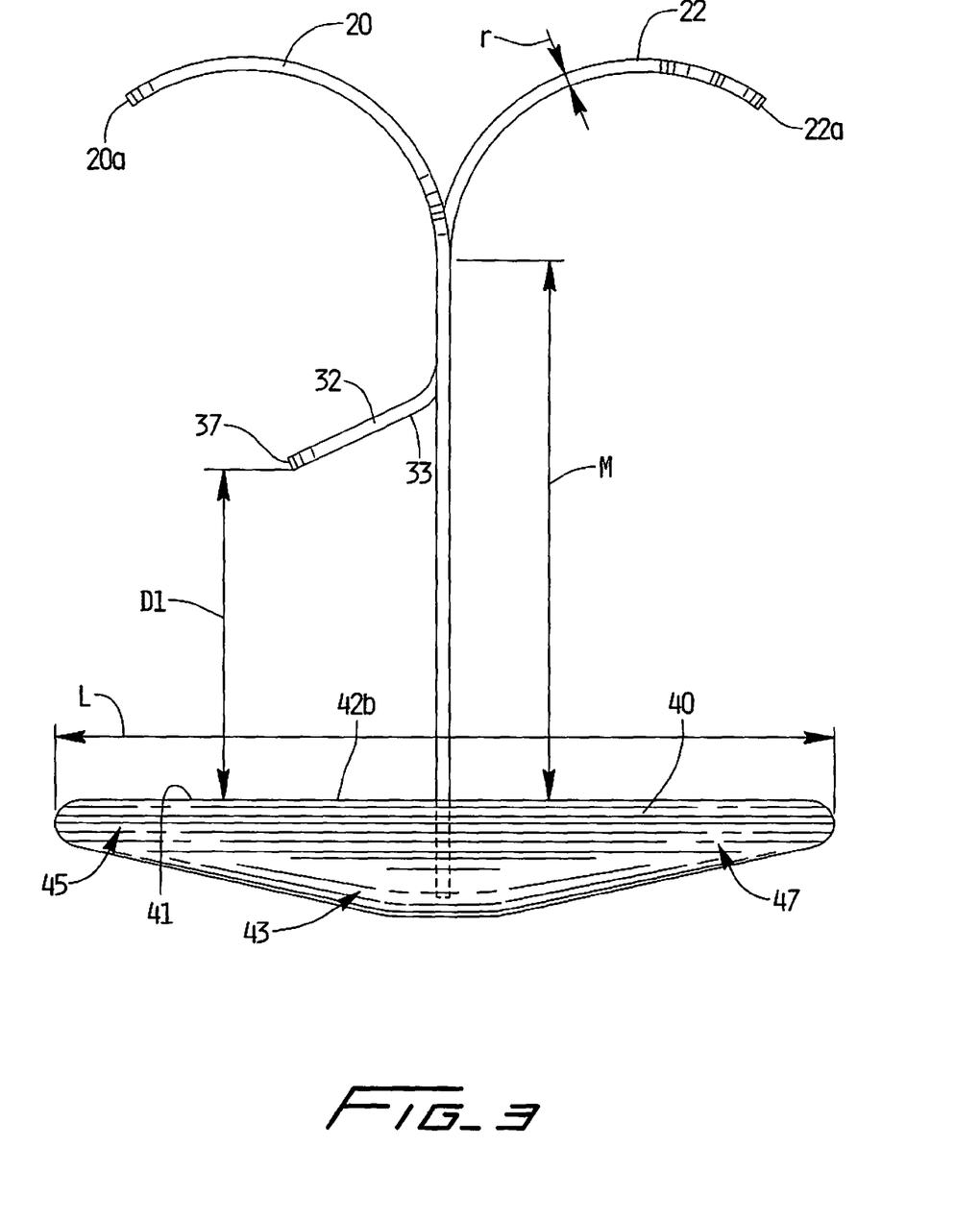
FIG. 3 is a side view of the closure device of FIG. 1.

The elongated covering member 40 functions to cover (patch) the internal opening in the vessel wall to prevent the egress of blood. With reference to FIGS. 1 and 3, the covering member 40 is oval shaped with elongated parallel side walls 42a, 42b and parallel end walls 44a, 44b connecting the side walls 42a, 42b. Although the ends preferably have straight wall portions 44a, 44b, curved walls are also contemplated. Covering member has a thicker region 43 in the central region than the first and second end regions 45, 47.

As noted above, clip legs 20 and 22 and retention tabs 30 and 32 of clip portion 11 are preferably composed of shape memory material, such as Nitinol (nickel titanium alloy). The memorized position is shown in FIG. 1. The clip portion is preferably fabricated from a single sheet, strip or ribbon of material by stamping, laser cutting or other processes. This flat sheet (or strip or ribbon) of material has a width p greater than its thickness r. In a preferred embodiment, the width p is about 0.050 inches and the thickness r is about 0.007 inches. The width q of each of the legs 20, 22 is preferably about 0.023 inches. Distal of the slot 27, in tab region 35, the width of the material preferably widens to a maximum width H (FIG. 2) of about 0.076 inches. Each tab 30, 32 preferably has a width J at its widest portion of about 0.026 inches. Other dimensions are contemplated.

Although two tabs and two legs are shown, alternatively, more than two legs, e.g. three or four legs, or a single leg, and more than two tabs or a single tab can all be formed from the metallic material. Also, the legs need not be symmetrically spaced with respect to one another nor need to curve in opposite directions. The tabs need not extend in the same direction.

Figure 1A:
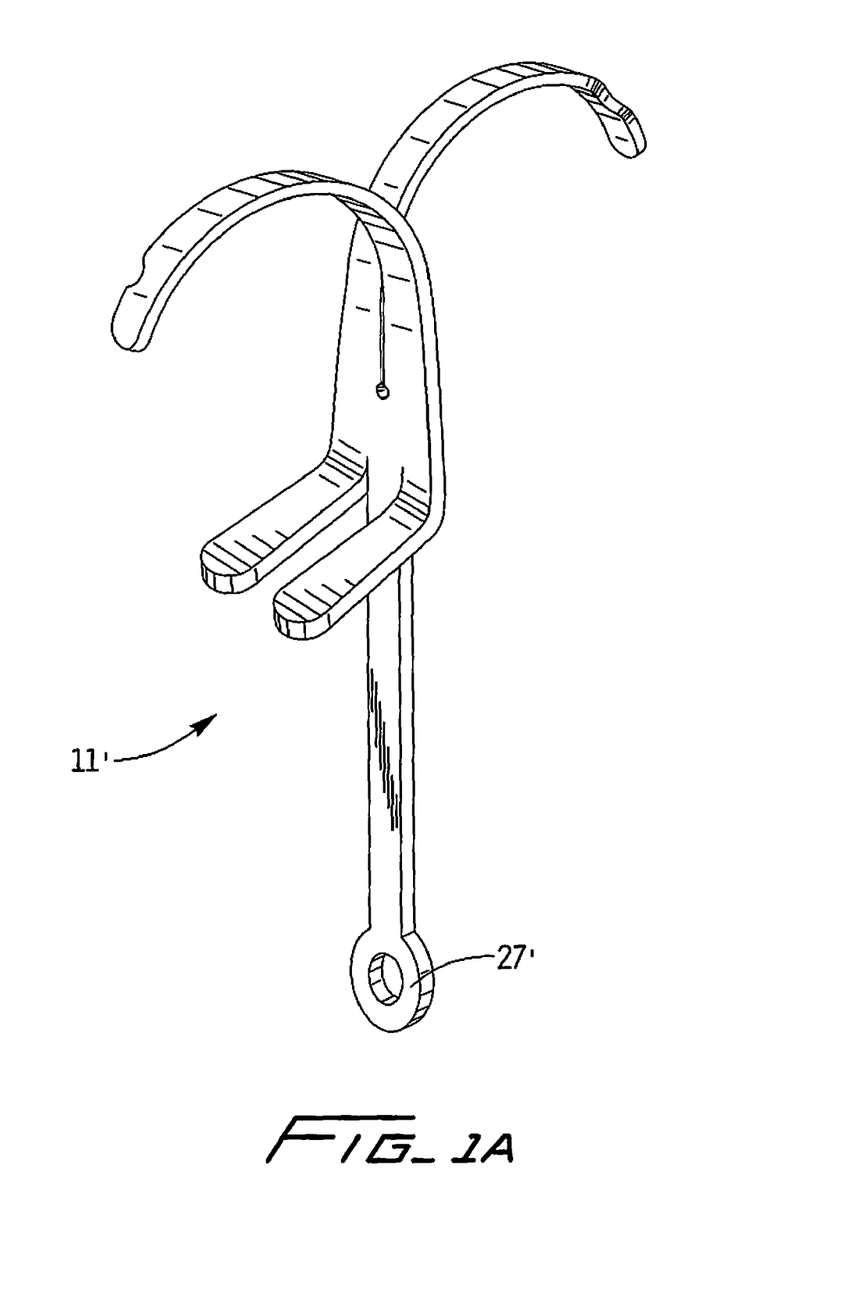
FIG. 1A is a perspective view of the clip portion of a second embodiment of the closure device of the present invention.

Elongated slot 27 divides the material into the two clip legs 20, 22 so the legs can curve in opposite directions. Each of the legs 20, 22 curves outwardly as shown, respectively has blunt distal ends 20a, 22a and contains a notch 28, 29 near the proximal end, which together form a pin receiving opening (described below) when the legs are in their straightened delivery configuration. The tabs 30, 32 separate at region 35. The connecting region of the material (spaced from the leg region) forms an enlarged head or connection tab 26 for attachment to the covering member (patch) 40. That is, the covering member 40 is molded over the enlarged connection head 26 to attach the clip portion 11 to the covering member 40. Although a triangular shaped connection head is shown, other shaped connecting heads are contemplated, such as a ring 27' of clip portion 11' shown in FIG. 1A, which creates an enlarged region to increase the surface area to improve retention when the covering member is molded over the connecting head. Further, shapes such as ring 27' improve the ability of the head to pull out of the vessel after resorbtion of the covering member.

Figure 2:
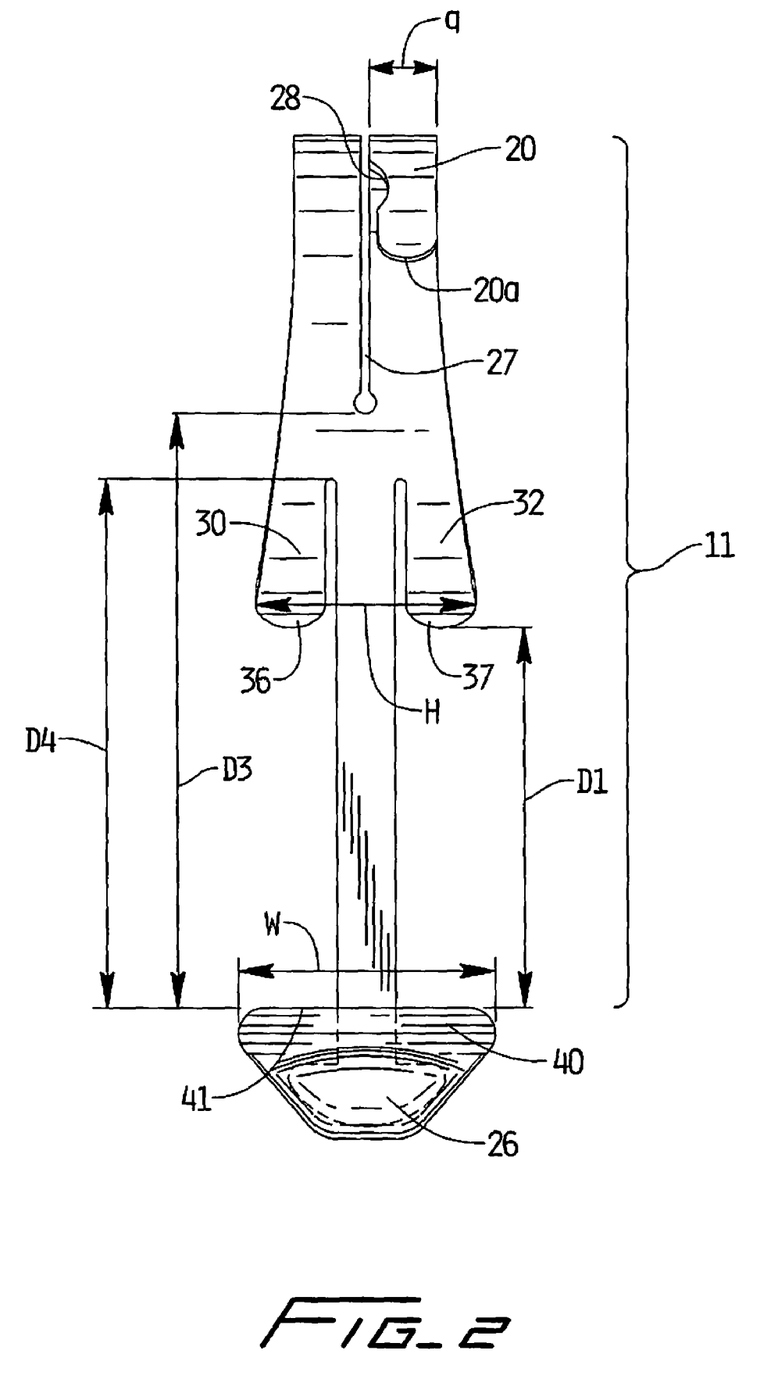
FIG. 2 is a front view of the closure device of FIG. 1.

As noted above, when the clip legs 20 and 22 are released from the delivery instrument, they are warmed by body temperature to curve as shown in FIGS. 1-3. The extent to which the clip legs can return to this memorized position will depend on the thickness and resistance of the tissue (and may also subsequently depend on the resporbtion of the patch). Once curved, the clip legs 20 and 22 grasp the tissue to retain the closure device 10 within the tissue and apply a proximal pulling force on the covering member 40 to pull it slightly upwardly (proximally) against the vessel wall. The legs may gather and force tissue toward the vessel wall. The retention tabs 30 and 32 prevent movement of the clip towards the vessel. That is, the bottom surface 31, 33 of tabs 30, 32, respectively, presses against the external wall of the vessel or against tissue seated atop the vessel wall, substantially parallel to the vessel wall. The tabs 30, 32 are spaced a sufficient distance from the covering member, e.g., about 2 mm during delivery, to ensure they are outside the vessel opening so they can move toward their flexed (memorized) position. Their memorized position is preferably about 2.79 mm from the covering member 40 as represented by distance D1 in FIGS. 2 and 3. Other dimensions are contemplated. The tabs 30, 32 limit further movement of the clip 10 towards the vessel and helps to prevent the covering member 40 from separating from the vessel wall (e.g. moving in the direction toward the opposing vessel wall) which could create an unwanted gap between the covering member 40 and the opening to allow blood flow. Tabs 30, 32 preferably have blunt tips 36, 37.

The longitudinal axis of covering member 40 defines a lengthwise dimension L and transverse axes define widthwise dimensions. The widthwise dimension w of the covering member 40 is preferably about 2.5 mm (for a 6 Fr device). Other dimensions are also contemplated. The width w preferably is at least substantially equal to the dimension of the internal opening in the vessel wall to effectively cover the opening.

It should be appreciated that alternatively the covering member could be provided with an enlarged width region as illustrated in the embodiment of FIG. 1 of the '141 application. The covering member could also be configured asymmetrically so that the enlarged region is off-centered to accommodate widening of the aperture as the member is pulled at an angle. The covering member could also be configured in a paddle shaped with a narrowed region adjacent a wider region as in FIGS. 9B-9E of the '141 application. Other covering member configurations including those disclosed in the '141 application could be utilized with the clip of this present application.

The elongated covering member can be composed of materials such as polycarbonate or polyurethane, or alternatively and preferably is composed of resorbable materials such as lactide/glycolide copolymers that after a period of time resorb in the body, leaving only the clip portion external of the vessel lumen. If composed of resorbable material, the covering member could optionally have regions of varying resorbability. Varying degrees of resorbability can be achieved by utilizing different materials having differing resorbable characteristics or by varying the thickness of the regions of the covering member (the thicker regions taking a longer time to resorb).

In a preferred embodiment, the covering member 40 has a length of about 8 mm (in a 6 French system) and the length of the clip portion 11 in the straightened delivery configuration is also about 9 mm (measured from the top surface 41 of the covering member 40). The slot 27 in this preferred embodiment begins at a distance D3 of about 4.5 mm from the top surface 41 of the covering member 40. The tabs 30, 32 in this embodiment begin at region 35, a distance D4 (FIG. 2) of about 4 nm from the top surface 41 of covering member 40. It should be appreciated that these dimensions are for one preferred embodiment as other dimensions are clearly also contemplated. The dimensions may also differ for other French size systems.

Figures 6, 6A:
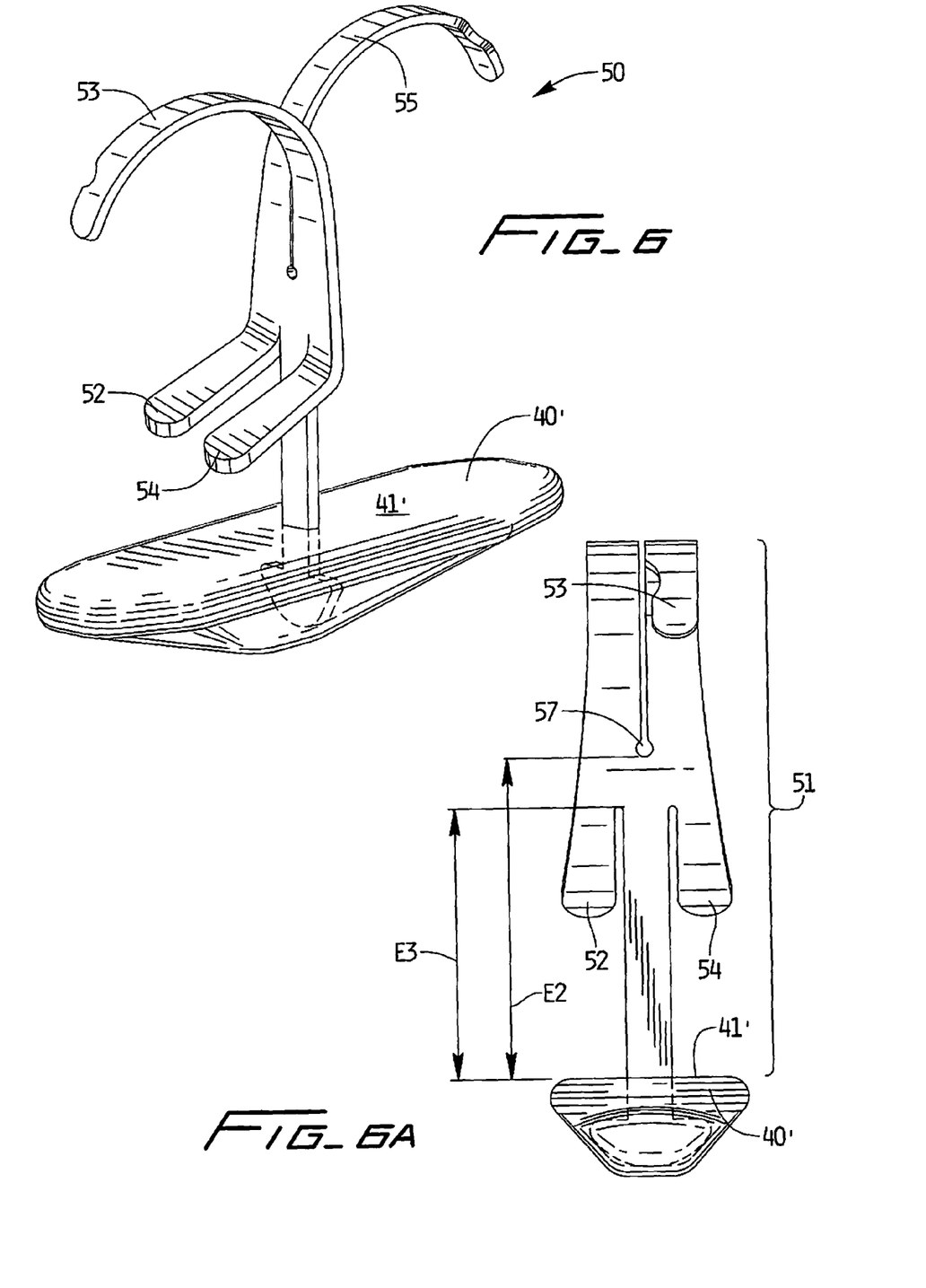
FIGS. 6, 6A and 7 are perspective, front and side views, respectively, of an alternate embodiment of the closure device of the present invention showing the clip legs and retention tabs in their memorized position.
Figure 7:
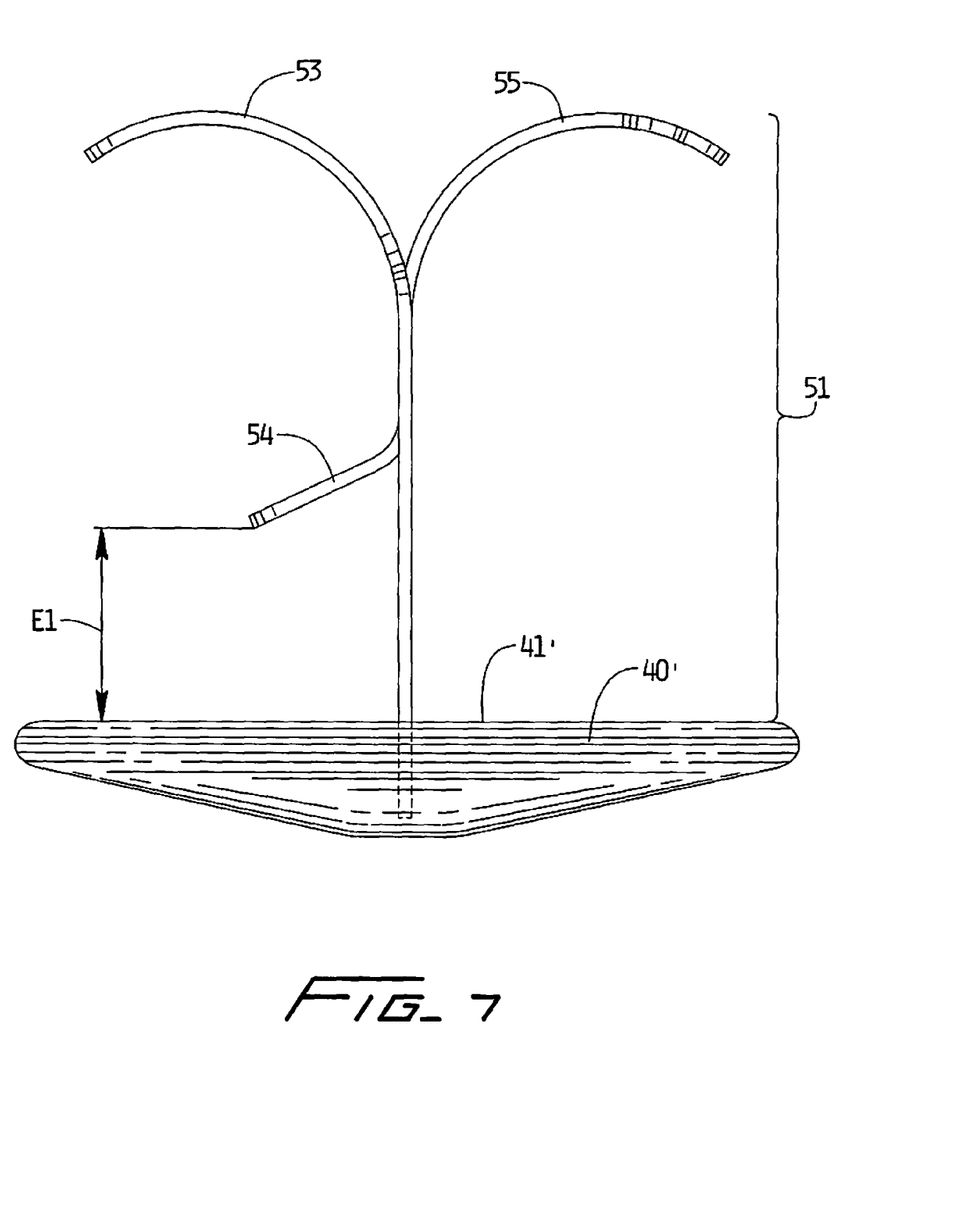

FIGS. 6 and 7 illustrate an alternate embodiment of the closure device of the present invention, designated generally by reference numeral 50. Closure device 50 is identical to closure device 10 except for the length of the clip portion 51 between the legs 43, 55/tabs 52, 54 and the top surface 41' of the covering member 40'. This distance E1 from the top surface 41' of covering member 40' to the tip of the tabs 52, 54 in the memorized position is preferably abut 1 mm; in the substantially straightened position for delivery the distance is preferably about 0.43 mm. The distance E3 from the top surface 41' to the tab region is preferably about 2.16 mm. The distance E2 from slot 57 to top surface 41' is preferably about 2.6 mm. The length of the clip portion 51 in the substantially straightened delivery configuration is preferably about 8 mm.

Figures 8, 9:
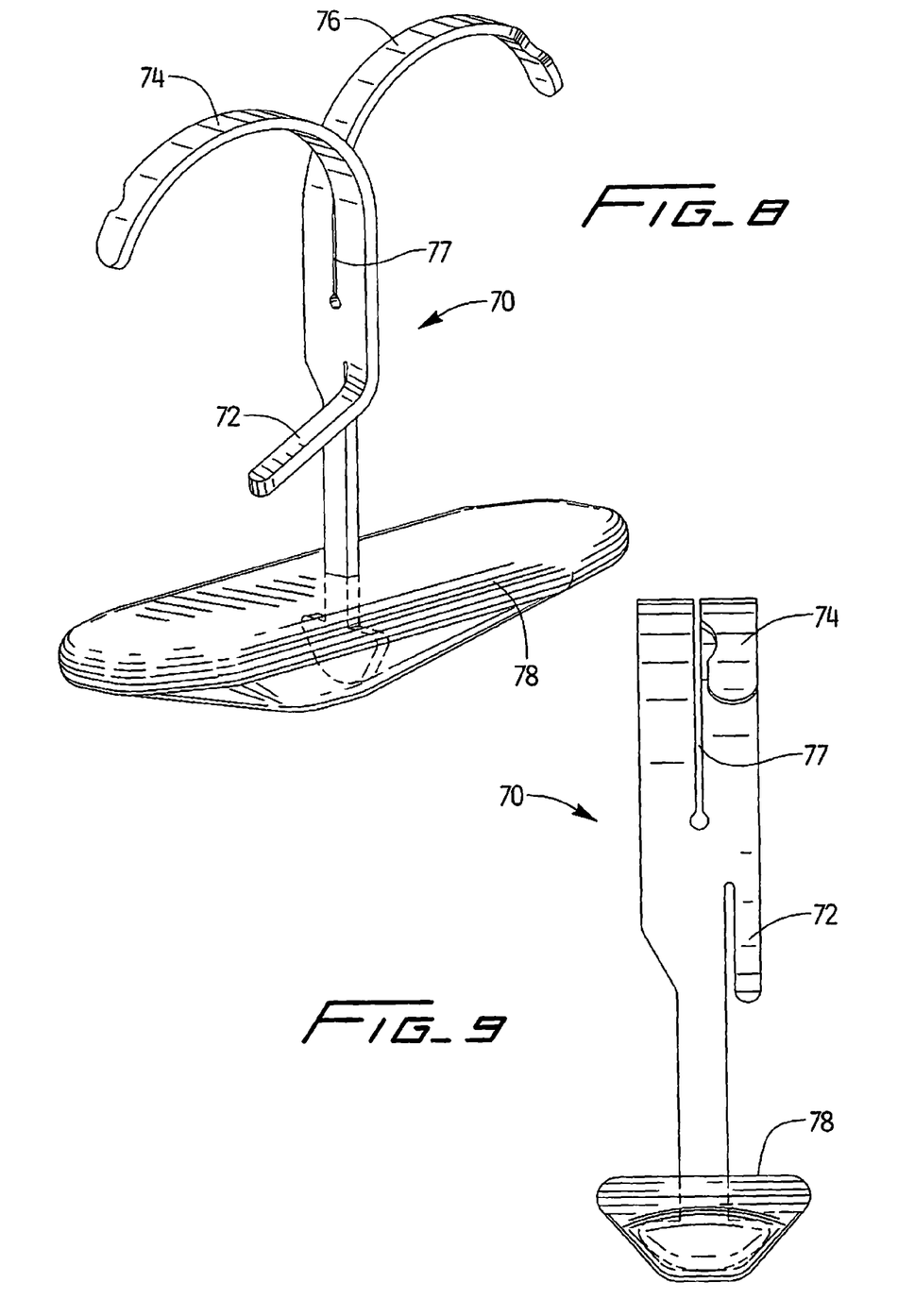
FIGS. 8 and 9 are perspective and front views, respectively, of another alternate embodiment of the closure device of the present invention showing the clip legs and the retention tab in the memorized position.

FIGS. 8 and 9 illustrate an alternate embodiment of the closure device of the present invention, designated by reference numeral 70. Closure device 70 is identical to closure device 10 except for the provision of a single tab 72 instead of two tabs. In all other respects, the closure device is the same as device 10 of FIG. 1 as it has, e.g., two curved legs 74, 76 separated by slot 77 and an elongated covering member 78.

Figure 5:
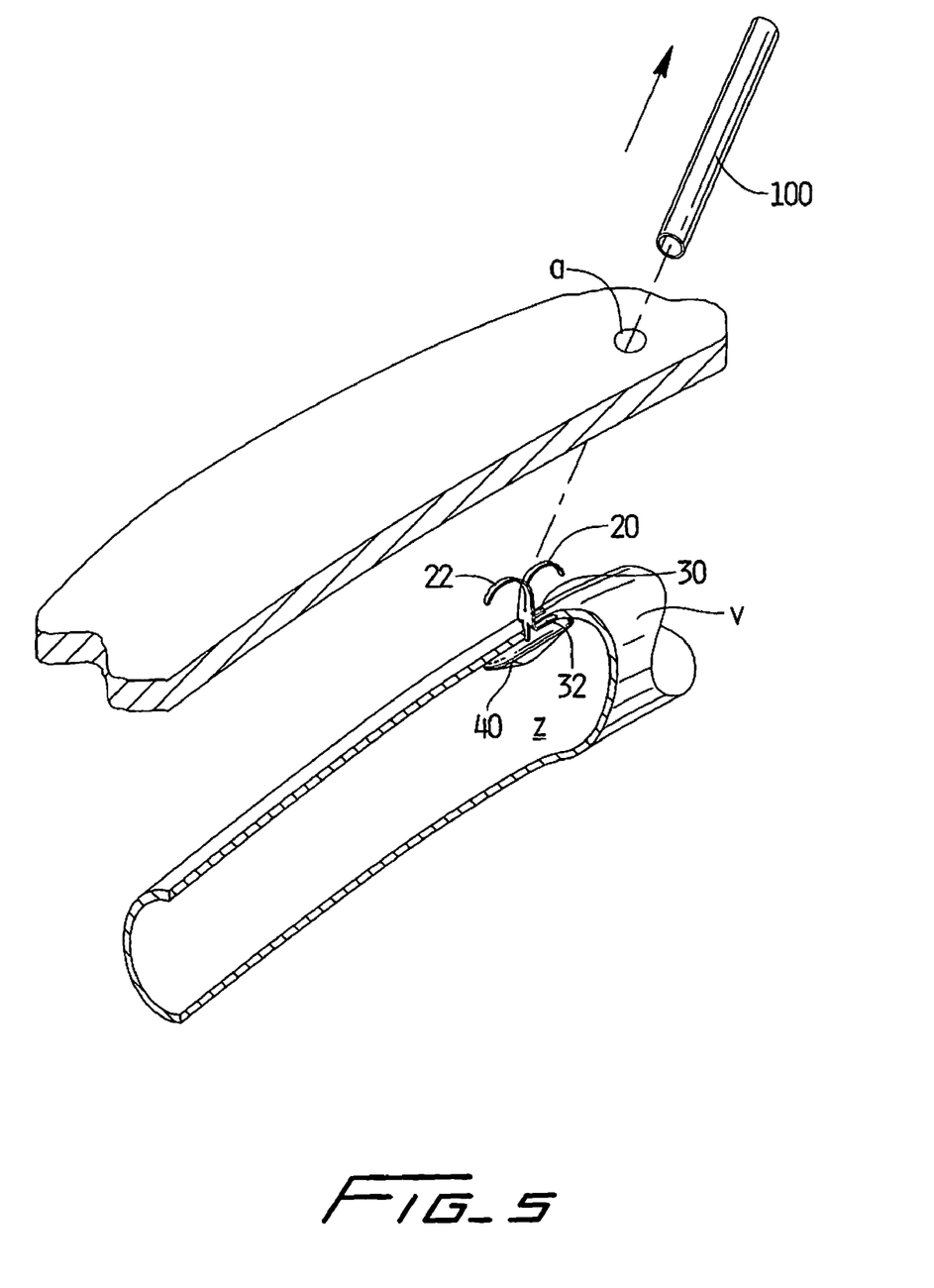
FIG. 5 is a perspective showing a portion of the vessel cut away to illustrate placement of the closure device of FIG. 1 in the vessel opening, the clip legs and retention tabs being shown in the memorized position and the surrounding tissue not shown for clarity.

FIG. 5 illustrates the placement of the closure device of FIG. 1 in the vessel after the delivery instrument is withdrawn. The other closure devices would be inserted and placed in a similar manner. As shown in FIG. 5 covering member 40 abuts the internal opening on the internal side of the vessel V to cover (patch) the opening and the curved legs 20, 22 curve outwardly from axis M (FIG. 3) towards the tissue tract and aperture to engage the tissue and apply a proximal (upward) force on the elongated covering member 40. Retention tabs 30, 32 engage the external surface of the vessel wall or engage tissue abutting external surface of the vessel wall, depending on the tissue thickness, to limit movement of the patch into the vessel. The other clips described herein can be delivered and placed in a similar manner.

The delivery instrument extends through opening "a" in the skin, through the tissue tract to the vessel V, through an external opening in the vessel wall, through the aperture in the vessel wall, and through an internal opening on the internal side of the vessel wall into the vessel lumen Z to deliver the closure device.

Figure 4B:
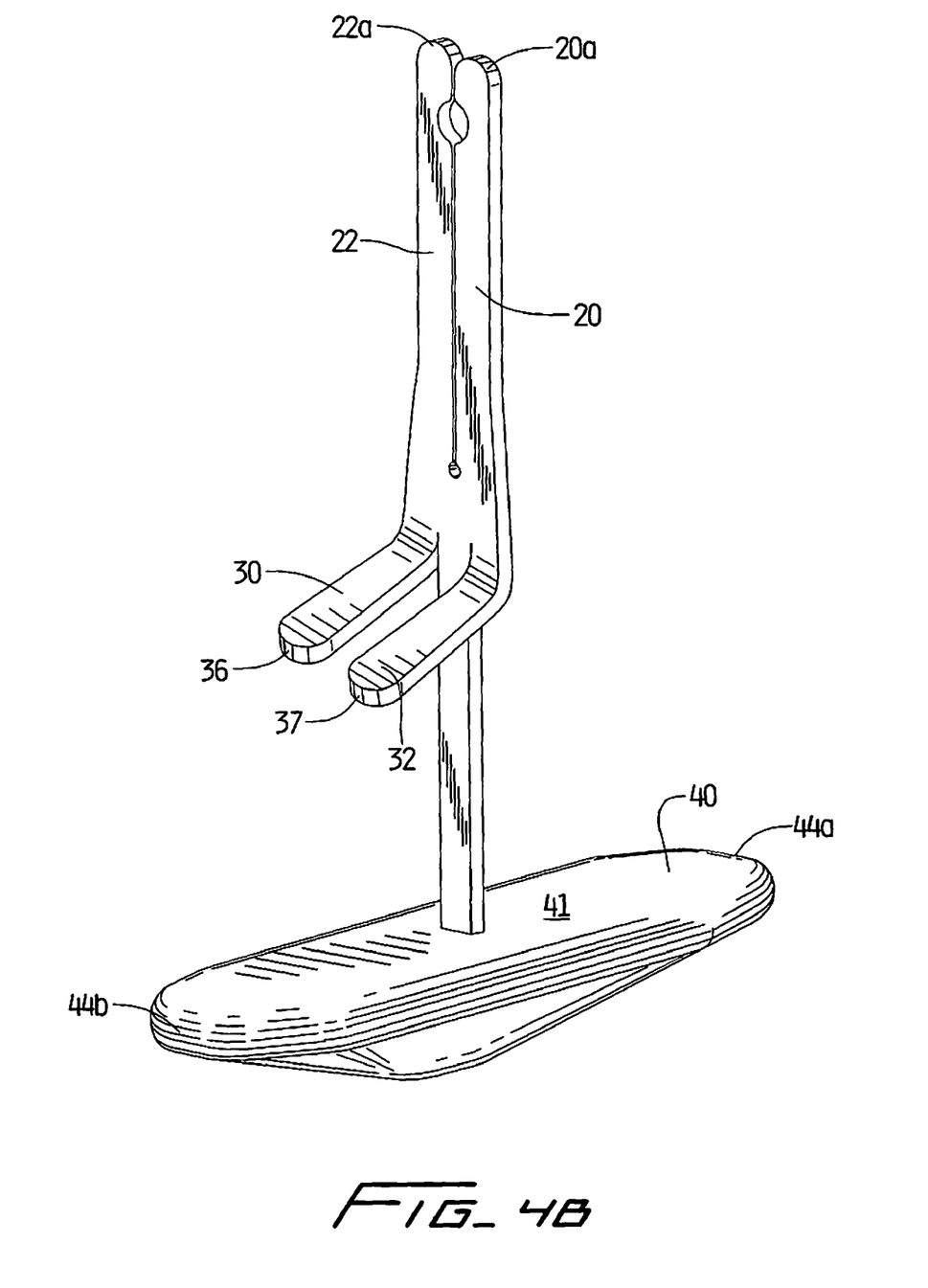
FIG. 4B is a perspective view showing the closure device of FIG. 1 in a partially delivered position.

For delivery, covering member 40 is ejected by a pusher (not shown) contacting wall 44a (see FIG. 4A). As shown, in this delivery position tabs 30, 32 overlie top surface 41 of covering member 40. Once covering member 40 is deployed from the delivery instrument and positioned within the vessel, the closure device is further released from the delivery instrument so the clip legs 20, 22 are warmed by body temperature and move towards their memorized configuration. Note, as shown in FIG. 4B, the retention tabs 30, 32 are released when the covering member 40 is released. Release enables tabs 30, 32, to angle outwardly as they are warmed by body temperature and move toward their memorized configuration so they are transverse to an axis M (see FIG. 3) which is transverse to the longitudinal axis L of the covering member 40. As shown, they preferably form an acute angle with axis M so they angle toward the covering member 40.

One method of deploying the clip legs is described in detail and illustrated in FIGS. 37A-37D in the '141 application and involves the release of the notches 28, 29 of clip legs 20, 22 from the clip engagement pin of the delivery system. The user pulls the sheath, delivery tube, and pusher proximally thereby pulling the covering member 40 against the internal opening of the vessel aperture to cover the opening in a patch-like manner spanning the internal opening to prevent egress of fluid through the aperture. Once engaged with the aperture and abutting the internal vessel wall, further retraction of the sheath, delivery tube, and pusher is countered by the force of the vessel wall against the covering member 40 until the force exceeds that of the clip engagement pin of the pusher. At that point, notches 27, 29 will disengage from the pin as the proximal ends of the clip legs are cammed outwardly. Thus, further retraction releases the clip legs from the delivery tube and sheath. Once the legs are released, they are warmed by body temperature and move toward their curved position to retain the covering member 40.

Note as an alternate, tabs 30, 32 can be released subsequent to release of the covering member, then followed by release of the legs 20, 22 in a separate step by further withdrawal of the delivery instrument. Alternatively, the clip legs 20, 22, and tabs 30, 32 can be released substantially simultaneously so the entire clip portion is released substantially simultaneously after deployment of the covering member.

Note that although FIG. 4 shows the legs and tabs in the fully memorized position, it should be appreciated that the extent they move to this position will depend on the tissue. Also, in FIG. 4, for clarity, the tissue is not shown which the clip legs would engage. Also, a portion of the vessel has been cut away to illustrate the covering member 40 positioned therein.

In each of the embodiments described herein, although blunt tips are illustrated, alternately sharpened (tissue penetrating) tips can be provided on the clip legs to perform their retention function. Instead of the notches formed in the clip legs, the legs could have bent delivery delivery tabs at their tips which curve inwardly toward the widened region of the clip portion. The delivery tabs function to retain the clip legs during delivery and allow subsequent release. The delivery tabs could be offset (non-symmetrical) with respect to each other. The ends of the legs could have widened areas to increase the surface area of tissue engagement. Further, barbs can be provided on the clip portion, e.g., the legs, tabs, etc., to provide additional retention.

In an alternate embodiment, rather than being perpendicular, the clip portion (containing the clip legs, tabs and connecting portion) can be positioned at an angle to the covering member. The angle could be about 45 degrees although other angles are contemplated.

Although preferably composed of shape memory metal, the clip legs can alternatively be composed of a shape memory plastic, stainless steel, resorbable material, or other materials. It should also be appreciated that the clip legs shown herein represent their full formation, e.g. their memorized position, when formed without any tissue resistance. When placed in tissue, the tabs and clip legs would not necessarily move (curve) to the full extent shown. The extent of their movement or curve would depend in large part on the type and thickness of the patient's tissue.

To facilitate passage of the shape memory clip legs and tabs through the lumen of the delivery instrument and into the vessel, cold saline is injected into the delivery instrument and around the legs and tabs in their collapsed position within the delivery instrument. The cold saline maintains the temperature dependent legs and tabs in a relatively softer more flexible condition as they are in the martensitic state within the delivery instrument. This facilitates their exit from the delivery instrument as frictional contact between the legs and tabs and the inner surface of the instrument is reduced.

While the above description contains many specifics, those specifics should not be construed as limitations on the scope of the disclosure, but merely as exemplifications of preferred embodiments thereof. The clip portion and covering member could be a multiple piece construction or the two clip legs could be positioned with respect to the covering member 90 degrees out of phase from FIG. 1. Those skilled in the art will envision many other possible variations that are within the scope and spirit of the disclosure as defined by the claims appended hereto.

What is claimed is:

1. A device for closing an aperture in a vessel wall, the aperture having an external opening in an external region of the vessel wall and an internal opening in an internal region of the vessel wall, the device comprising:
    a covering member having a longitudinal axis and positionable inside the vessel against the internal opening of the aperture, the covering member having a dimension to prevent egress of fluid through the aperture, the covering member having a length with a dimension greater than a dimension of the width and movable between a first position for delivery and a transverse position for placement, in the placement position the covering member having an upper surface extending along the length and positioned adjacent the aperture;
    two curved legs having portions positionable external of the vessel, the legs having a delivery configuration and a placement configuration, the legs curving in different directions and extending toward the upper surface of the covering member in the placement configuration, and terminating in free ends, the legs extending in an elongated substantially straightened position in the delivery configuration; and
    at least one retention member positioned between the covering member and curved legs and positionable external of the vessel, the at least one retention member spaced from the covering member, the at least one retention member movable from a delivery configuration to a placement configuration wherein the at least one retention member extending a first transverse distance, the first transverse distance being less than the dimension of the length of the covering member.

2. The device of claim 1, wherein the two curved legs and the at least one retention member are fabricated from a unitary material.

3. The device of claim 1, wherein the at least two curved legs and at least one retention member are composed of shape memory metal material.

4. The device of claim 1, wherein the curved legs are fabricated from a material which separates at a first region to form the legs and the material includes a connection region, spaced distally from the first region to connect the curved legs to the covering member.

5. The device of claim 4, wherein the legs are fabricated of metal material and the covering member is fabricated of a polymeric material molded over the metal material.

6. The device of claim 1, wherein the covering member is composed of a resorbable material.

7. The device of claim 3, wherein the covering member is composed of a resorbable material.

8. The device of claim 1, further comprising a second retention member positioned between the covering member and curved legs and positionable external of the vessel.

9. The device of claim 8, wherein the retention members extend at an angle to an acute axis transverse to a longitudinal axis of the covering member.

10. The device of claim 9, wherein the retention members extend in substantially the same direction.

11. The device of claim 1, wherein the at least one retention member extends at an acute angle to an axis transverse to a longitudinal axis of the covering member.

12. The device of claim 1, wherein the at least one retention member is composed of shape memory material and has a memorized position extending transverse to an axis transverse to a longitudinal axis of the covering member.

13. The device of claim 1, wherein the at least one retention member extends at an angle toward the covering member to limit movement of the device into the vessel once the device is positioned to close the aperture in the vessel wall.

14. The device of claim 13, wherein the retention member is composed of shape memory material and is delivered in a substantially straightened position.

15. The device of claim 14, wherein the curved legs are composed of shape memory material and the covering member is composed of a resorbable material.

* * * * *